United States Patent [19]

Ohno et al.

[11] 4,017,647
[45] Apr. 12, 1977

[54] METHOD FOR PROVIDING ENTERIC COATINGS ON SOLID DOSAGE FORMS

[75] Inventors: Shigeru Ohno, Kamakura; Noboru Hoshi, Higashikurune; Fujio Sekigawa, Yono, all of Japan

[73] Assignee: Shin-Etsu Chemical Company Limited, Tokyo, Japan

[22] Filed: June 9, 1975

[21] Appl. No.: 584,914

[30] Foreign Application Priority Data

June 11, 1974 Japan ............................ 49-66271

[52] U.S. Cl. ..................... 427/3; 424/33; 424/35
[51] Int. Cl.$^2$ .................. A61K 9/00; A61K 15/00; A61K 21/00
[58] Field of Search .............. 427/3, 339, 341; 424/33, 35

[56] References Cited

UNITED STATES PATENTS

| | | | |
|---|---|---|---|
| 3,030,273 | 4/1962 | Zagnoli | 424/35 |
| 3,196,827 | 7/1965 | Wurster et al. | 427/3 |
| 3,256,111 | 6/1966 | Singiser | 427/3 |
| 3,303,051 | 2/1967 | Paul | 427/339 |
| 3,420,931 | 1/1969 | Daum et al. | 424/35 |
| 3,427,182 | 2/1969 | Zingerman | 427/3 |
| 3,573,966 | 4/1971 | Hostetler | 427/3 |
| 3,896,108 | 7/1975 | Klug | 424/35 |

*Primary Examiner*—Ronald H. Smith
*Assistant Examiner*—S. Silverberg
*Attorney, Agent, or Firm*—Toren, McGeady and Stanger

[57] ABSTRACT

Enteric coatings are provided on solid pharmaceutical dosage forms by a method comprising covering the dosage froms with an aqueous solution of a polymeric substance having carboxyl groups in the watersoluble salt form and contacting the thus coated dosage forms with an inorganic acid to convert the polymeric substance into the water-insoluble acid form. The coating solution includes no organic solvent, and this method is safe from dangers of fires or explosions and air pollution.

13 Claims, No Drawings

METHOD FOR PROVIDING ENTERIC COATINGS ON SOLID DOSAGE FORMS

FIELD OF THE INVENTION

This invention relates to an improved method for providing enteric coatings on solid pharmaceutical dosage forms.

DESCRIPTION OF THE PRIOR ART

The provision of enteric coatings on solid pharmaceutical dosage forms, such as, tablets, pills, granules, capsules and the like has been carried out by a method comprising coating the dosage forms with various enteric-coating materials dissolved in an organic solvent with the addition, if necesary, of plasticizers and coloring agents. This method is disadvantageous from both the economical and safety viewpoints due to the use of a large amount of expensive solvents for the preparation of the coating solutions and the risk of fires or explosions during the coating operation. A further disadvantage of the method is that air pollution is caused by the vapor of the organic solvent which is discharged during the coating operation, most of which is released into the atmosphere, since it is much too diluted with air to be cooled below its dew point by the usual cooling means, condensed, be collected and recovered. Attempts have sometimes been made to collect and recover the hazardous solvent vapor with the aid of an adsorbent, such as active charcoal, but the use of the adsorbent proved to be very costly and is not always effective in obtaining satisfactory results.

OBJECTS OF THE INVENTION

It is therefore the principal object of this invention to provide an improved method for providing enteric coatings on solid pharmaceutical dosage forms which is free of the above-described disadvantages and difficulties and, for the purpose, characterized by the absence of organic solvents in the formulation of the coating solutions. Another object is to provide a method which has no adverse effects on any of the active ingredients of the dosage forms.

SUMMARY OF THE INVENTION

In order to attain the objects of this invention, a method is proposed which is based on the discovery that enteric coatings can be provided on solid pharmaceutical dosage forms by coating the dosage forms with an aqueous solution of a polymeric substance having carboxyl groups in the water-soluble salt form and bringing the thus coated dosage forms into contact with an inorganic acid to convert the polymeric substance into the acid form which is insoluble in water.

DETAILED DESCRIPTION OF THE INVENTION

The polymeric substances useful for the method of this invention are of the class containing carboxyl groups in their molecules and are insoluble in water or an acid of any concentration so long as the whole or most of the carboxyl groups are in acid form, but become water-soluble when the whole or most of the carboxyl groups have been converted into the salt form with an alkali metal, ammonium or an amine, and also soluble in the normal small-intestinal juice having a strong buffer capacity in the pH range of from 4 to 8.

Illustrative of the polymeric substances are (1) partial esters of at least one cellulose derivative having one or more substitution groups, such as, an alkyl cellulose (for example, methyl cellulose or ethyl cellulose), a hydroxyalkyl cellulose (for example, hydroxyethyl cellulose or hydroxypropyl cellulose), a hydroxyalkyl alkyl cellulose (for example, hydroxyethyl methyl cellulose, hydroxyethyl ethyl cellulose, or hydroxypropyl methyl cellulose), or cellulose esters (for example, cellulose acetate and cellulose acetate butyrate partially retaining hydroxyl groups of cellulose), with at least one polybasic acid, such as, succinic acid, maleic acid, phthalic acid, tetrahydrophthalic acid, hexahydrophthalic acid, trimellitic acid, or pyromellitic acid; (2) partial esters of at least one vinyl polymer or copolymer containing in its molecules vinyl alcohol units (for example, partially saponified polyvinyl acetate or polyvinyl acetoacetal) with at least one of the above-mentioned polybasic acids; (3) polymers of polymerizable monomers having carboxyl groups, such as, acrylic acid or methacrylic acid, or copolymers involving such a monomer unit; (4) polymeric substances convertible into the acid form by hydrolysis, such as, the polymers or copolymers of acrylic or methacrylic esters; and (5) polymers or copolymers prepared from monomers having carboxyl groups in the salt form, such as, sodium acrylate which are sodium methacrylate and readily convertible into the acid form.

Among the above-mentioned examples of the polymeric substances, the polymers or copolymers prepared from monomers having carboxyl groups in the salt form, as is, may be dissolved in water, while the other polymeric substances in the acid form must have their carboxyl groups converted into salts with alkali metals, ammonia, or amines by reacting them with alkali metal hydroxides, such as, sodium hydroxide and potassium hydroxide, ammonium hydroxide or amines, such as, triethanol amine, to obtain an aqueous solution that is suitable for coating in accordance with this invention. In this case, a sufficient amount of carboxyl groups must be present in the polymeric substance so that the salt of the polymer thus prepared may be soluble in water.

To prepare the suitable aqueous coating solution from the polymer of the acid form, it is preferred from the commercial point of view as well as the ease of the operation, to first put the polymer into water followed by stirring during the addition of a basic substance, such as, an alkali metal hydroxide, ammonia water or an amine, in an amount sufficient to convert the polymeric substance into a salt form and at the same time dissolve it in water. It is of course possible to dissolve the salt of the polymeric substance prepared in advance in water or dissolve the polymeric substance of acid form while it is converted into the salt form in an aqueous solution containing the base substance in a stoichiometric amount.

The aqueous solution of a salt of polymer thus prepared usually has a pH value of from 4 to 8. However, a higher value of pH which is naturally brought about by the presence of an excess amount of the base, does not hinder the practice of the method of this invention. The concentration of the aqueous solution is not particularly limited, but it may be determined in most cases according to the capacity of the coating machine employed, the nature of the solid dosage forms to be coated and the kind of the polymeric substance.

To the aqueous solution thus prepared may be added, if necessary, water-soluble film-forming materials, such as, water-soluble cellulose ethers, polyvinyl alcohol, polyethylene glycol, gelatin, or those materials which are dispersed in water, such as, emulsions of polyvinyl acetate or vinylacetate containing copolyers and of polymers or copolymers of acrylic esters. However, care should be taken so that the amount of the water-soluble film-forming materials should be within limits which do not adversely affect the enteric property of the polymeric substance, say, the insolubility in gastric juice and solubility in intestinal juice. The ratios in which the carboxyl-containing polymeric substance and water-soluble film-forming material are mixed vary, depending upon the kinds of the water-soluble film-forming materials used but, generally speaking, the amount of the water-soluble film-forming material should not exceed 30% by weight based on the weight of the carboxyl-containing polymeric substance with the convertibility from the salt form to the acid form or vice versa. Besides the film-forming materials, coloring agents, flavorings, titanium dioxide, edible lake pigments, and other body pigments, such as, talc and fine-powdered silica may be added optionally to the polymeric substance.

Any conventional coating machines, for example, pan coaters, rotary drum-type coaters, such as, Accela-Cota manufactured by Manesty Machines, England, Wurster-type fluidizing coaters developed by Wisconsin Alumuni Research Foundation, U.S.A., and fluidizing coaters such as that manufactured by Glatt, West Germany, may be employed in the method of the invention. There is no difference in principle between the conditions with which the solid dosage forms are coated in accordance with the invention and those with which the abovementioned conventional coaters are operated using a coating solution with an organic solvent. The characteristic advantage of the method according to this invention using a coating solution without an organic solvent lies in that there is no danger of fires or explosions and air or environmental pollution to be caused by evaporation of the solvents.

The thickness of the coating film should be determined depending upon the following factors including the kinds of the polymeric substances employed, the kinds of other materials added, the ratio in which the polymeric substance and other materials are mixed, the pH value of intestinal juice, disintegration time in intestinal juice desired, and the extent to which the penetration of gastric juice into the film is permitted. In most cases, the thickness of the film ranging from 0.01 to 0.5 mm will serve the purpose, although it is not limited thereto. According to the invention, the solid dosage forms thus coated with the polymeric substance of the salt form are brought into contact with an acid so that the polymeric substance is converted into the acid form. The acid suitable for the purpose is selected from strong inorganic acids, including hydrochloric acid, sulfuric acid, and phosphoric acid. The acids are usually used in the form of diluted acids and in some cases, in the form of hydrous or anhydrous gases. Although the concentration of the acid to be used and the contact time required vary depending on the thickness of the coating film, it is an example that when the acid has a concentration of 1 N, the contact time will be from 3 to 30 minutes. Further, the amount of the acid to be used must be equal to or larger than the equivalent amount of the polymeric substance in the salt form used, and is from 1.1 to 50 times the equivalent, though not limited thereto.

As the result of its contact with the acid, the polymeric substance in the salt form is converted to the acid form while the alkali or amine combined therein is washed out of the coating as a salt with the acid. Any acid employed in excess can also be washed away with water, if necessary. However, if the presence of the acid or salt does not reduce the effectiveness of the drug or decrease the pharmaceutical acceptance of the drug, it is not required to wash the acid-treated solid dosage forms.

The coated solid dosage forms in accordance with the method of this invention as described above possess satisfactory enteric properties, in most cases, are finished by drying in any conventional manner.

It should be added that the enteric coated solid dosage forms are optionally overcoated with sugar or other materials or polished according to any known methods. It is also optional that the solid dosage forms are subjected to undercoating with conventional coating materials before they are treated with the enteric coating in accordance with the method of this invention.

The following examples are illustrative of the method of this invention and are not to be construed as limiting. In the examples, parts and percentages are all based on weight.

EXAMPLE 1

Tablets containing potassium chloride as an active ingredient were manufactured by the following procedure.

A mixture of 100 parts of potassium chloride and 15 parts of a 10% aqueous solution of gelatin was kneaded well and then extruded by means of an extrusion granulator. The resulting product was dried at 50° C for 6 hours in a drying chamber with a circulating air current. To the dried granules was added 0.5 part of calcium stearate, followed by mixing, and the mixture was fed to a rotary tablet machine to make tablets, 9 mm in diameter and 350 mg in weight per tablet.

The tablets thus manufactured and not yet coated were found completely disintegrated within a period of from 10 minutes and 30 seconds to 12 minutes and 30 seconds when tested by the method of disintegration test for "uncoated tablets" in accordance with the U.S. Pharmacopoeia, 18th Revision (hereinafter referred to as "U.S.P. XVIII").

On the other hand, a coating solution was prepared by the following procedure. 10 parts of hydroxypropyl methylcellulose phthalate, product of Shin-Etsu Chemical Co., Ltd., Japan (tradename: HPMCP, Type:HP-55), containing 6.8% of hydroxypropyl groups, 19.7% of methoxy groups, and 33.8% of carboxybenzoyl groups were dispersed in 80 parts of water and, with the addition of 0.85 part of sodium hydroxide dissolved in 10 parts of water, the mixture was stirred for about 30 minutes, to obtain the desired clear coating solution.

Then, using the tablets and coating solution obtained above, coating operations were conducted by the following procedure.

Into a coating pan made of reinforced polyester resin were put 2 kg of the tablets, and the coating operations were conducted by spraying the solution kept at 50° C by means of a spray gun for 8 seconds and blowing air heated at 60° C for 30 seconds over the tablets. This procedure was alternately repeated over a period of 5 hours. The thus coated tablets had a coating film 0.13 mm thick and a beautiful appearance with smooth and glossy surfaces.

The coated tablets thus obtained were subjected to the following two methods of acid treatment.

The method used an acid solution. The coated tablets were immersed in 5 liters of 4 N hydrochloric acid (at 20° C) with stirring for 20 minutes and thereupon were washed in a current of deionized water till the water became neutral according to methyl orange indicator. The washed tablets were then dried in a drying chamber with a circulating air current at 60° C for 3 hours. The thus treated tablets had a beautiful appearance with smooth and glossy surfaces.

These tablets were subjected to the disintegration test for "enteric-coated tablets" in accordance with U.S.P. XVIII. It was found that the tablets remained unchanged by the simulated gastric fluid test which lasted for 1 hour, but they were completely disintegrated by the simulated intestinal fluid test subsequently carried out within a period of from 16 minutes and 35 seconds to 18 minutes and 55 seconds.

For comparison, tablets coated but not treated with the acid solution were subjected to the same disintegration test and, as a result, were found to be completely disintegrated or to have most of their contents dissolved out in the simulated gastric fluid. The result shows that those tablets do not satisfy the requirements for enteric coated solid dosage forms.

The other method of acid treatment was one using hydrogen chloride gas. The coated tablets were put into a glass tube 10 cm in diameter and a dry hydrogen chloride gas kept at 20° C was passed therethrough at the rate of 300 ml/min. for 30 minutes. Thereupon, a current of deionized water was applied through the tube to wash the tablets inside until it became neutral as indicated methyl orange indicator. The washed tablets were then dried in a drying chamber with a circulating air current at 50° C for 5 hours. The thus treated tablets had a beautiful appearance with smooth and glossy surfaces.

These tablets were subjected to the disintegration test for enteric-coated tablets in accordance with U.S.P. XVIII and, as a result, were found to remain unchanged by the simulated gastric fluid test and to be completely disintegrated by the simulated intestinal fluid test subsequently carried out within a period of from 16 minutes and 30 seconds to 18 minutes and 40 seconds.

EXAMPLE 2

Tablets containing aspirin as an active ingredient were manufactured by the following procedure.

A mixture of 90 parts of aspirin in the granular form, 5 parts of corn starch, and 5 parts of calcium carboxymethylcellulose, product of Daicel Limited, Japan (tradename: ECG-505) was compressed into tablets by means of a rotary tablet machine to form tablets, 9 mm in diameter and 300 mg in weight per tablet.

The tablets thus manufactured and not yet coated were found completely disintegrated within a period of from 1 minute and 20 seconds to 1 minute and 35 seconds when tested by the method of disintegration test for uncoated tablets in accordance with U.S.P. XVIII.

On the other hand, a coating solution was prepared by the following procedure.

10 parts of cellulose acetate phthalate, product of Wako Junyaku Co., Ltd., Japan, containing 20.3% of acetyl groups and 34.6% of carboxybenzoyl groups, was dispersed in 70 parts of water and, with the addition of 0.9 part of sodium hydroxide dissolved in 10 parts of water and 1 part of polyethylene glycol, 4000 dissolved in 10 parts of water, the mixture was stirred for about 30 minutes, to obtain the desired clear coating solution.

Then, using the tablets and coating solution obtained above, coating operations were conducted as follows.

Into a fluidizing coater of the Wurster type (4 inches in inside diameter) was put 1.3 kg of the tablets, and the coating operations were conducted by use of the coating solution under the following conditions.

Temperature of the coating solution—25° C
Temperature of fluidizing air—60° C
Spray rate of the coating solution—8 ml/min.
Coating time—125 min.

As a result, there were obtained tablets having coatings 0.14 mm thick.

The coated tablets thus obtained were then subjected to the same acid-treatment using an acid solution, followed by washing and drying as in Example 1.

The thus treated tablets were subjected to the disintegration test for enteric-coated tablets in accordance with U.S.P. XVIII. The test result indicated that the tablets remained unchanged in the simulated gastric fluid and were completely disintegrated in the simulated intestinal fluid within a period of from 6 minutes and 40 seconds to 7 minutes and 10 seconds.

For comparison, tablets coated but not given the acid treatment, were put to the same disintegration test and, as a result, were found to be disintegrated or to have most of their contents dissolved out in the simulated gastric fluid. The result means that these tablets do not satisfy the requirements for enteric-coated solid dosage forms.

EXAMPLE 3

A coating solution with which the same tablets as obtained in Example 2 would be coated was prepared by the following procedure.

To a solution of 0.65 part of sodium carbonate in 88 parts of water was added 10 parts of hydroxypropyl methylcellulose phthalate, product of Shin-Etsu Chemical Co., Ltd., Japan (tradename: HPMCP; type: HP-50), containing 7.9% of hydroxypropyl groups, 23.4% of methoxy groups, and 22.8% of carboxybenzoyl groups, and the mixture was stirred for about 30 minutes. To the resultant solution was added 0.15 part of Sunset Yellow FCF aluminum lake dispersed in 2 parts of water, and the resultant dispersion was stirred for about 5 minutes to obtain the desired coating solution.

Using the above coating solution and tablets, coating operations were conducted by charging 3 kg of the tablets in a coater of the Accela-Cota type having a drum 40 cm in diameter, spraying the coating solution maintained at 50° C at the rate of 10 ml/min., and supplying air heated at 60° C over a period of 4 hours, to form coatings 0.14 mm thick. The tablets were given a beautiful appearance with smooth and glossy surfaces.

The coated tablets obtained above were then subjected to an acid-treatment using hydrochloric acid as follows.

The coated tablets were immersed in 7 liters of 3 N hydrochloric acid (at 20° C) with stirring for 10 minutes and thereupon subjected to washing in a current of deionized water till the water became neutral according to the methyl orange indicator. The washed tablets were then dried in a drying chamber with a circulating air current maintained at 50° C for 3 hours. The thus treated tablets had a beautiful appearance with smooth and glossy surfaces.

These tablets were then subjected to the disintegration test for enteric-coated tablets in accordance with U.S.P. XVIII. The test result indicated that the tablets remained unchanged in the simulated gastric fluid and were completely disintegrated in the siumlated intestinal fluid within a period of from 4 minutes and 50 seconds to 5 minutes and 30 seconds.

For comparison, tablets coated but not given the acid treatment were put to the same disintegration test and, as a result, found to be disintegrated or to have most of their contents dissolved out in the simulated gastric fluid. The result means that these tablets do not satisfy the requirements for enteric-coated solid dosage forms.

EXAMPLE 4

Granules containing aspirin as an active ingredient were manufactured by the following procedure.

To a mixture consisting of 70 parts of aspirin and 30 parts of lactose were added 20 parts of a 15% solution of polyvinyl pyrrolidone (K-30) in isopropanol. The resulting mixture was well kneaded and then extruded through an extruder with a screen mesh having an aperture 1.0 mm wide to produce granules. The granules thus obtained were dried in a drying chamber with a circulating air current at 40° C for 5 hours.

On the other hand, a coating solution for coating the above granules was prepared by the following procedure.

To a dispersion of 8 parts of the same hydroxypropyl methylcellulose phthalate as used in Example 1 in 80 parts of water was added 0.68 part of sodium hydroxide dissolved in 10 parts of water, and the mixture was stirred for about 30 minutes. To the resultant solution was added 0.15 part of Tartrazine aluminum lake dispersed in 2 parts of water, and the resultant dispersion was stirred for about 5 minutes to obtain the desired coating solution.

Using the above coating solution and granules, coating operations were conducted by means of a fluidizing coater WSG-5 of Werner Glatt, Germany under the following conditions.

Temperature of the coating solution—25° C
Temperature of fluidizing air—65° C
Spraying rate of the coating solution—150 ml/min.
Coating time—80 min.

The amount of the hydroxypropyl methylcellulose phthalate used in the coating was 0.9 kg, equivalent to 18% of the total weight of the uncoated granules.

The coated granules obtained above were then subjected to an acid-treatment using hydrochloric acid as follows.

The coated granules were immersed in 20 liters of 5 N hydrochloric acid (at 20° C) with stirring for 10 minutes and thereupon subjected to washing in a current of deionized water till the water became neutral according to the methyl orange indicator. The washed granules were then dried in a drying chamber with a circulating air current maintained at 45° C for 5 hours.

These granules were then subjected to the disintegration test, using an apparatus in accordance with the Japanese Pharmacopoeia, 8th Revision and the same testing solutions, i.e., simulated gastric and intestinal fluids, as used in U.S.P. XVIII. The test result indicated that the granules remained unchanged in the simulated gastric fluid in an hour and were completely disintegrated in the simulated intestinal fluid within a period of from 4 minutes and 10 seconds to 4 minutes and 50 seconds.

For comparison, granules coated but not given the acid treatment were put to the same disintegration test and, as a result, found to be disintegrated or to have most of their contents dissolved out in the simulated gastric fluid. This means that these granules do not satisfy the requirements for enteric-coated granules.

What is claimed is:

1. A method for providing an enteric coating on a solid pharmaceutical dosage form which comprises coating said dosage form with an aqueous solution of a polymeric substance having carboxyl groups in the form of a water-soluble salt selected from the group consisting of alkali metal, ammonium and amine salts of said polymeric substance said coating being carried out in the absence of an organic solvent and bringing the coated dosage form into contact with a strong inorganic acid so that said polymeric substance is converted into a water-insoluble acid form, the amount of said acid being equal to or greater than the equivalent amount of said salt.

2. The method as claimed in claim 1 wherein said polymeric substance is a partial ester of at least one cellulose derivative selected from the class consisting of cellulose ethers and cellulose esters with at least one polybasic acid.

3. The method as claimed in claim 1 wherein said polymeric substance is selected from the class consisting of partial esters of at least one vinyl polymer or copolymer containing vinyl alcohol units in its molecules with at least one polybasic acid and polymers or copolymers of vinyl monomers having carboxyl groups.

4. The method as claimed in claim 2 wherein said cellulose ether is selected from the class consisting of methyl cellulose, ethyl cellulose, hydroxyethyl cellulose, hydroxypropyl cellulose, hydroxyethyl methyl cellulose, hydroxyethyl ethyl cellulose, and hydroxypropyl methyl cellulose.

5. The method as claimed in claim 2 wherein said cellulose ester is selected from the class consisting of cellulose acetate and cellulose acetate butyrate.

6. The method as claimed in claim 2 wherein said polybasic acid is selected from the class consisting of succinic acid, maleic acid, phthalic acid, tetrahydrophthalic acid, hexahydrophthalic acid, trimellitic acid, and pyromellitic acid.

7. The method as claimed in claim 1 wherein said inorganic acid is hydrochloric acid, sulfuric acid, or phosphoric acid.

8. The method as claimed in claim 7 wherein said hydrochloric acid is in gaseous form.

9. The method as claimed in claim 2 wherein said partial ester is cellulose acetate phthalate.

10. The method as claimed in claim 2 wherein said partial ester is hydroxypropyl methyl cellulose phthalate.

11. The method as claimed in claim 1 wherein said coating layer has a thickness in the range from 0.01 to 0.5 mm.

12. A method for providing an enteric coating on a solid pharmaceutical dosage form which comprises coating said solid dosage form with an aqueous solution of cellulose acetate phthalate in a water-soluble sodium salt form in the absence of organic solvent to form a layer of from 0.01 to 0.5 mm thick and bringing the coated dosage form into contact with hydrochloric acid in an amount in excess over the equivalent of said sodium salt of cellulose acetate phthalate whereby said sodium salt of cellulose acetate phthalate is converted into a water-insoluble acid form.

13. A method for providing an enteric coating on a solid pharmaceutical dosage form which comprises coating said solid dosage form with an aqueous solutin of hydroxypropyl methyl cellulose phthalate in a water-soluble sodium salt form in the absence of an organic solvent to form a layer of from 0.01 to 0.5 mm thick and brining the coated dosage form into contact with hydrochloric acid in an amount in excess over the equivalent to said sodium salt of hydroxypropyl methyl cellulose phthalate whereby said sodium salt of hydroxypropyl methyl cellulose phthalate is converted into a water-insoluble acid form.

* * * * *